(12) United States Patent
Kindlein et al.

(10) Patent No.: US 8,133,166 B2
(45) Date of Patent: Mar. 13, 2012

(54) APPARATUS AND METHOD FOR EFFECTING RADIATION TREATMENT ON A PRE-SELECTED ANATOMICAL PORTION OF AN ANIMAL BODY

(75) Inventors: Johann Kindlein, Toenisvorst (DE); Arie Visscher, Driebergen (NL); Johan Henning, Veenendaal (NL); Wouter Peter Engels, Nieuwegein (NL)

(73) Assignee: Nucletron B.V., Veenendaal (NL)

( * ) Notice: Subject to any disclaimer, the term of this patent is extended or adjusted under 35 U.S.C. 154(b) by 1639 days.

(21) Appl. No.: 11/487,303

(22) Filed: Jul. 17, 2006

(65) Prior Publication Data
US 2007/0038205 A1  Feb. 15, 2007

(30) Foreign Application Priority Data

Jul. 18, 2005  (EP) .................................... 05076645
Jul. 14, 2006  (EP) .................................... 06014654

(51) Int. Cl.
*A61N 5/00* (2006.01)
(52) U.S. Cl. .......................................................... 600/3
(58) Field of Classification Search .................. 600/1–8; 250/496.1, 497.1
See application file for complete search history.

(56) References Cited

U.S. PATENT DOCUMENTS

| | | | | |
|---|---|---|---|---|
| 4,851,694 A * | 7/1989 | Rague et al. | ............. | 250/497.1 |
| 6,311,084 B1 | 10/2001 | Cormack et al. | | |
| 2002/0193677 A1 | 12/2002 | Thornton | | |

FOREIGN PATENT DOCUMENTS

| | | |
|---|---|---|
| EP | 1314451 | 5/2003 |
| EP | 1369143 | 12/2003 |
| EP | 1374949 | 1/2004 |
| EP | 1445002 | 8/2004 |
| EP | 1529533 | 5/2005 |

* cited by examiner

*Primary Examiner* — Charles A. Marmor, II
*Assistant Examiner* — Christine Hopkins
(74) *Attorney, Agent, or Firm* — Finnegan, Henderson, Farabow, Garrett & Dunner LLP

(57) ABSTRACT

The invention relates to an apparatus for effecting radiation treatment on a pre-selected anatomical portion of an animal body comprising: a group of n hollow treatment channels being inserted at one or more pre-planned positions in said pre-selected anatomical portion; a group of m delivery channels to be connected to a corresponding number m from said group of n hollow treatment channels with m being 2 or more and n being 1 or more; identifying means for identifying which one of said m delivery channels is being connected with which one of said n hollow treatment channels, said identifying means comprising a tracking element accommodated in a tracking channel, said tracking element being intended to be displaced from said tracking channel through each of said interconnected m delivery channels and m treatment channels; storage means for storing k energy emitting sources in a corresponding source-channel, with k≦m; delivery means for temporarily inserting said k energy emitting sources from their source-channels through a corresponding one of said interconnected m delivery channels and m treatment channels towards one of said pre-planned positions in said anatomical portion; coupling means for coupling at least one of said m delivery channels with a corresponding treatment channel.

26 Claims, 13 Drawing Sheets

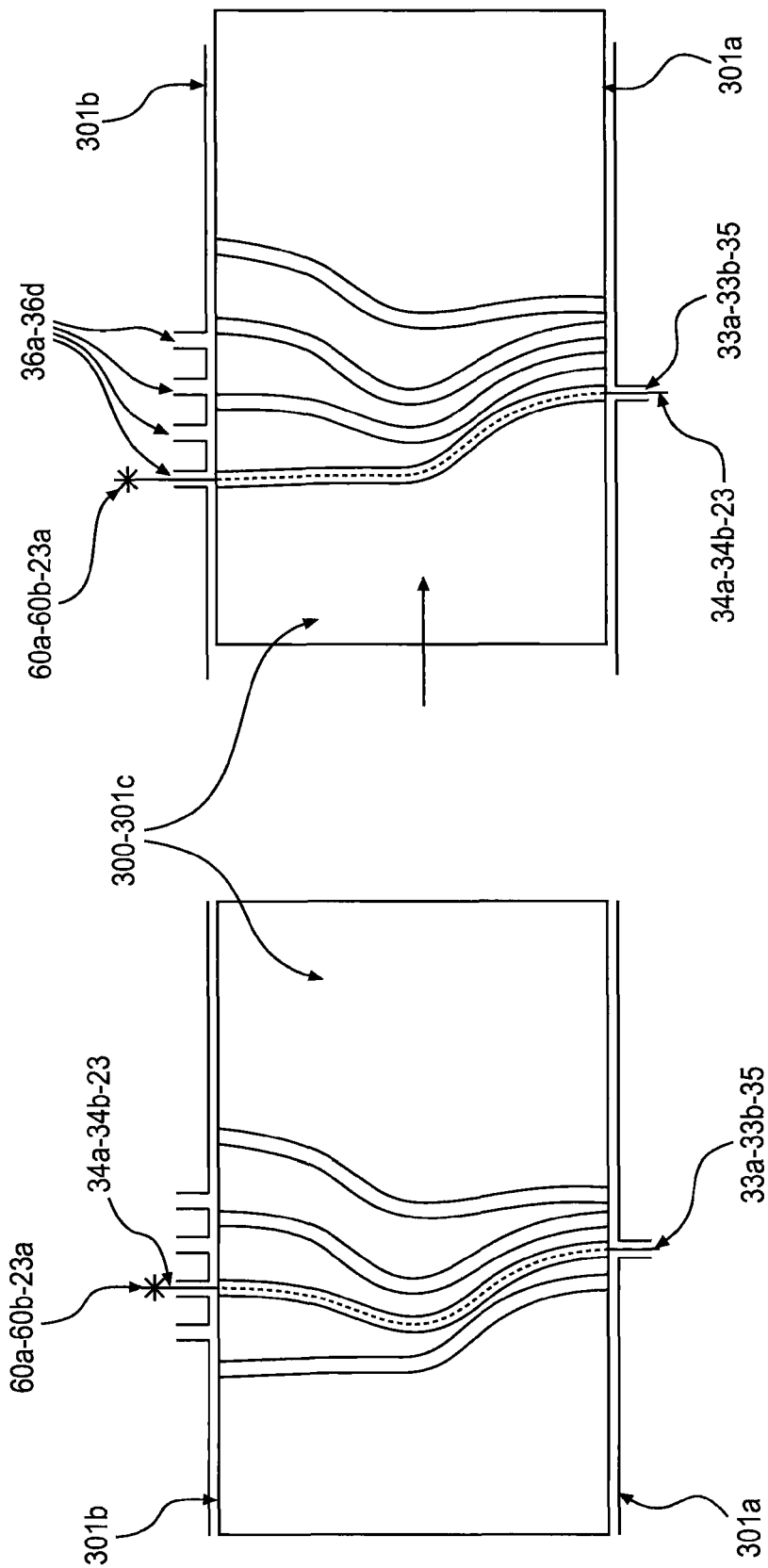

Figure 1:
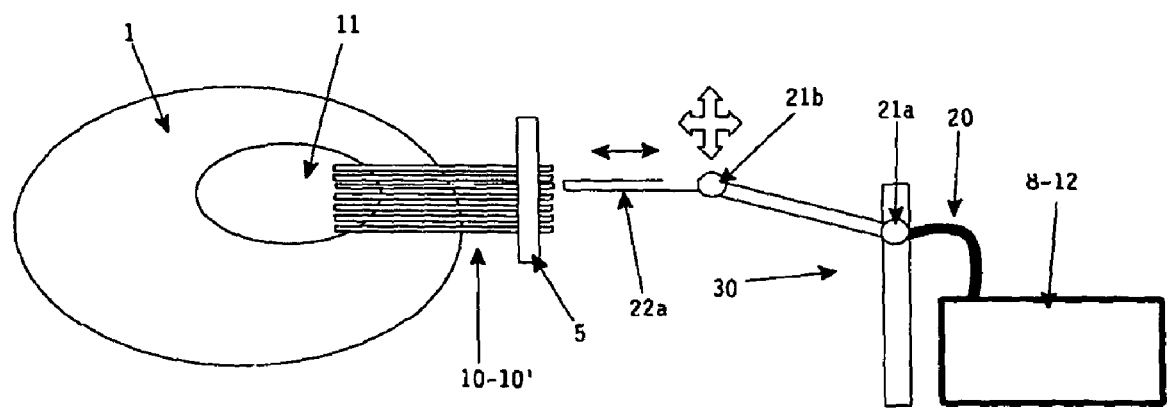

APPARATUS AND METHOD FOR EFFECTING RADIATION TREATMENT ON A PRE-SELECTED ANATOMICAL PORTION OF AN ANIMAL BODY

The invention relates to an apparatus for effecting radiation treatment on a pre-selected anatomical portion of an animal body comprising: a group of n hollow treatment channels being inserted at one or more pre-planned positions in said pre-selected anatomical portion; a group of m delivery channels to be connected to a corresponding number m from said group of n hollow treatment channels with m being 2 or more and n being 1 or more; identifying means for identifying which one of said m delivery channels is being connected with which one of said n hollow treatment channels, said identifying means comprising a tracking element accommodated in a tracking channel, said tracking element being intended to be displaced from said tracking channel through each of said interconnected m delivery channels and m treatment channels; storage means for storing k energy emitting sources in a corresponding source-channel, with k≦m; delivery means for temporarily inserting said k energy emitting sources from their source-channels through a corresponding one of said interconnected m delivery channels and m treatment channels towards one of said pre-planned positions in said anatomical portion; coupling means for coupling at least one of said m delivery channels with a corresponding treatment channel.

The invention also relates to a method for effecting radiation treatment on a pre-selected anatomical portion of an animal body comprising the steps of: I) inserting a group of n hollow treatment channels at one or more positions in said pre-selected anatomical portion; ii) permanently connecting with said group of n hollow treatment channels with a group of n connecting positions of a fixed positioned connecting template; iii) connecting a group of m delivery channels with a number m of said group of n connecting positions of the template; iv) inserting k energy emitting sources each through one of said m delivery channels and interconnected n hollow treatment channels towards one or more positions in said pre-selected anatomical portion.

Remote after loaders are devices generally used in the cancer treatment field to accurately advance and retract a flexible wire containing a gamma radiation emitting source over a specified distance for a specific time period. A remote after loader comprises a flexible simulation wire for testing purposes and a flexible wire with the gamma radiation emitting source, specific control and transport mechanisms to operate both types of wires, as well as a radiation shielded housing for the radiation emitting source.

Typically one or more catheters, needles or other closed pathways (hereafter "treatment channels" or "treatment needles") to the treatment site are positioned in the patient. The treatment channels are then attached to the after loader, which advances the radioactive source at the end of the transport wire, sometimes called a source wire, from a source storage channel through an interconnected delivery channel and a treatment channel, which is connected to said delivery channel.

The subsequent positioning of the energy emitting source through the interconnected delivery channels/treatment channels at the several positions in the tumour is performed according to a predetermined sequence calculated by a treatment planning system in order to deliver a correct therapeutic dose of radiation to the tumour.

The radiation (energy) emitting sources presently used are radioactive sources, which sources continuously emit gamma radiation following the principles of natural radioactive decay and which are characterized by the specific half life time of the used radioactive material. Since the sources used in such treatment can constitute a hazard to a user (doctor, physicist, nurse, etc.) performing the treatment, after loaders are used for inserting of the radioactive source in the patient with minimum radiation exposure of the technician or with no exposure whatsoever.

These after loader devices allow the insertion of the radioactive source in the patient after the user administering the treatment moves away from the patient or leaves the treatment room. In other words, the radioactive source is loaded into the patient for treatment after the user leaves the patient, and for that reason such devices are generally referred to as "remote after loading devices".

If large tumours have to be treated with brachytherapy the number hollow needles used and inserted into the patient's body (and hence in the tumour to be treated) can be high. With the increasing number of the treatment channels inserted into the tumour, the risk of false connections between the treatment channels and the delivery channels increases which results in a misadministration.

To this end an identification of the treatment channels and the interconnected delivery channel is performed in order to position the correct source via the correct delivery channel and treatment channel at the correct position within the tumour according to the pre-planned treatment plan.

A drawback of these prior art devices is that the source can be only moved out of the storage means towards a delivery channel/treatment channel after the dummy has checked the next treatment channels. This results in increased waiting time by a high number of treatment channels and extends the average treatment time for the patient (and hence increased discomfort).

A further disadvantage of the described system is that the patient is permanently connected with a large number of treatment channels and the tracking element (dummy source) is unable to detect automatically, whether the treatment channel is correctly connected with the delivery channel according to the treatment plan.

An example of a device described above is disclosed in the not yet published European patent application No. 05076645.0 in the name of the same applicant.

The invention aims to provide an apparatus according to the above preamble allowing a safer and more efficient treatment, reducing the risk of treatment errors and minimizing the discomfort to the patient.

According to the invention further delivery channel connecting means are arranged so as that by only one coupling position of the coupling means the k energy emitting sources can be inserted alternatively and simultaneously through the m delivery channels towards a first group of m treatment channels connected with said m delivery channels, whereas the m delivery and m treatment channels have been previously checked by the identification means.

Herewith a proper selection and interconnection of the multiple source channels together with the tracking channel with one or more delivery channels is accomplished, resulting in a more versatile apparatus allowing the temporary placement of multiple energy emitting sources via said specific delivery channels within a patient's body and simultaneously checking the correct identity of the next treatment channel in the pre-planned sequence of the therapy treatment and reducing the total waiting time.

Furthermore any discomfort to the patient is herewith reduced.

More in particular the delivery channel connecting means comprise a cylindrical shaped element, which cylindrical shaped element is rotatable about it longitudinal axis and provided with grooves, each groove interconnecting one of said m delivery channels with either one of said source-channels or said tracking channel.

In a preferred embodiment at least two of said grooves are shaped as straight grooves, whereas in another embodiment said straight grooves cross each other in a perpendicular manner.

As in a further embodiment furthermore at least a further groove is shaped as a curved groove a quick and versatile interconnection of one or more source channels as well as a tracking channel in a simultaneous manner with multiple delivery channels/treatment channels is accomplished, allowing the performance of multiple therapy treatments (by inserting multiple energy emitting sources through said treatment channels) as well as a proper identification of a further delivery channel/treatment channel for the next treatment session.

This will speed up the therapy treatment and reduce any discomfort to the patient.

More in particular said at least curved groove exhibits a ¼-quarter of the cylindrical circumferential surface.

In one embodiment said grooves are provided in an end face of said cylindrical shaped element extending perpendicular to the longitudinal axis of rotation, whereas in another embodiment said grooves are provided in the circumferential surface of said cylindrical shaped element extending substantially parallel to the longitudinal axis of rotation.

In another versatile embodiment the delivery channel connecting means comprise a shifting element, which can be displaced in lateral direction, and which shifting element is provided with grooves interconnecting one of said m delivery channels with either one of said source-channels or said tracking channel.

More in particular said grooves are shaped as straight grooves, wherein said grooves are inclined in view of the lateral displacement of the element.

For a correct and safe operation of the apparatus according to the invention connecting means are present for connection each of said m delivery channels with one of said corresponding number m hollow treatment channels.

More in particular said coupling means comprise a robotic arm carrying said m delivery channels and provided at its free end with a coupling element, which coupling element is adapted to be brought in engagement with a template to which said group of n hollow treatment channels are connected.

In order to minimize operation errors and to improve the safe environment for performing therapy treatment with multiple energy emitting sources the coupling means comprise at least one activatable sensing element present on the coupling element.

In a preferred embodiment the sensing elements consist of a pair of a light emitting element and a light receiving element, wherein another embodiment the coupling means comprise at least one electromagnet present on the coupling element for maintaining the coupling between the coupling element and the template during treatment.

In one preferred embodiment of the apparatus according to the invention k=2 and m=4.

The method according to the invention is further characterized in that step iii) comprises the step of v) selectively and alternatively connecting the m delivery channels with another number m of said group n connecting positions of the template connected with the treatment channels.

The invention also relates to a method for classifying an energy emitting source contained in an radiation shielded compartment and intended for insertion through an insertion channel towards a position in a pre-selected anatomical portion of an animal body comprising the steps of: a) displacing said energy emitting source from said radiation shielded compartment over a certain distance through said insertion channel with a shielded element; b) detecting the dose being delivered from said energy emitting source during said displacement over said certain distance at different points over that distance; c) determining the dose at said different point over that distance; d) comparing said determined dose measurements with one or more pre-determined and stored dose-distance curves.

Figure 2:
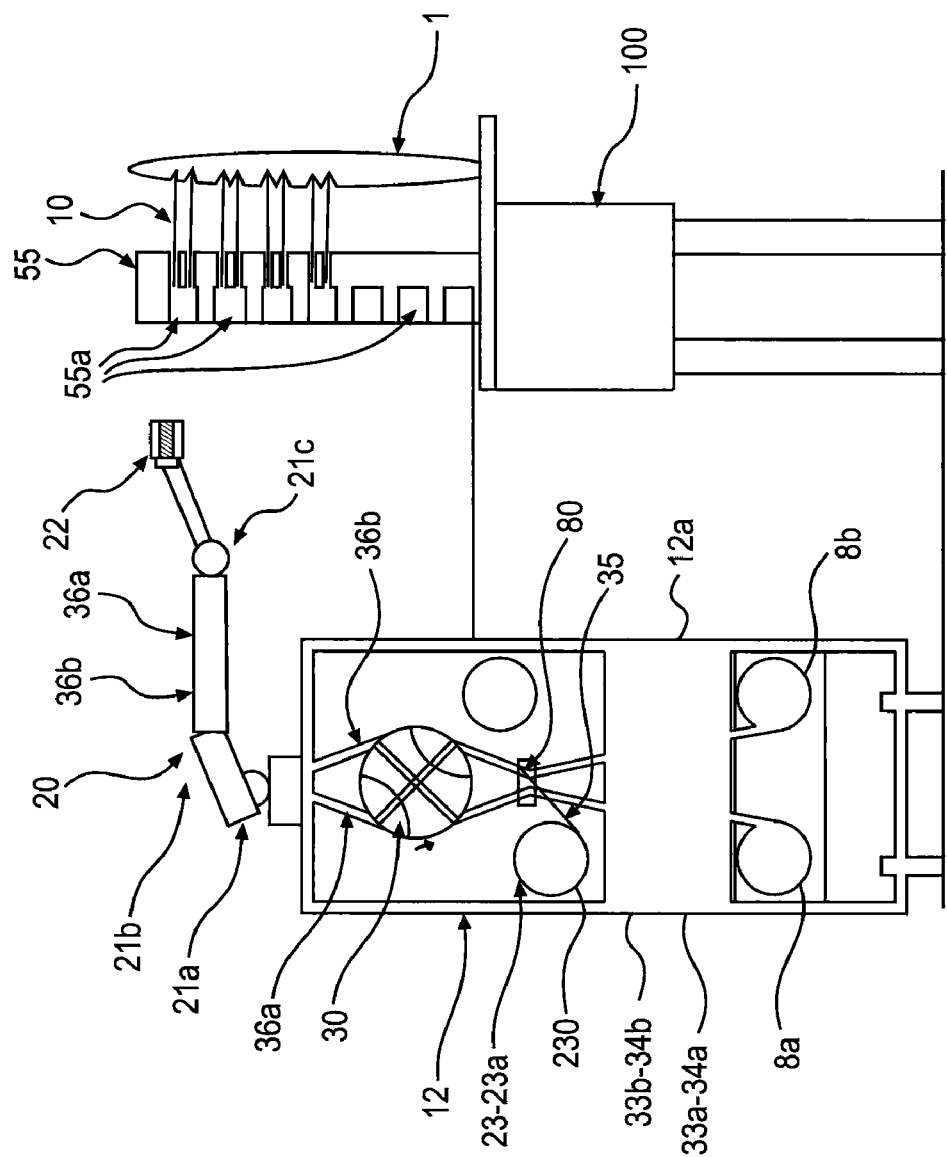
Figure 3A:
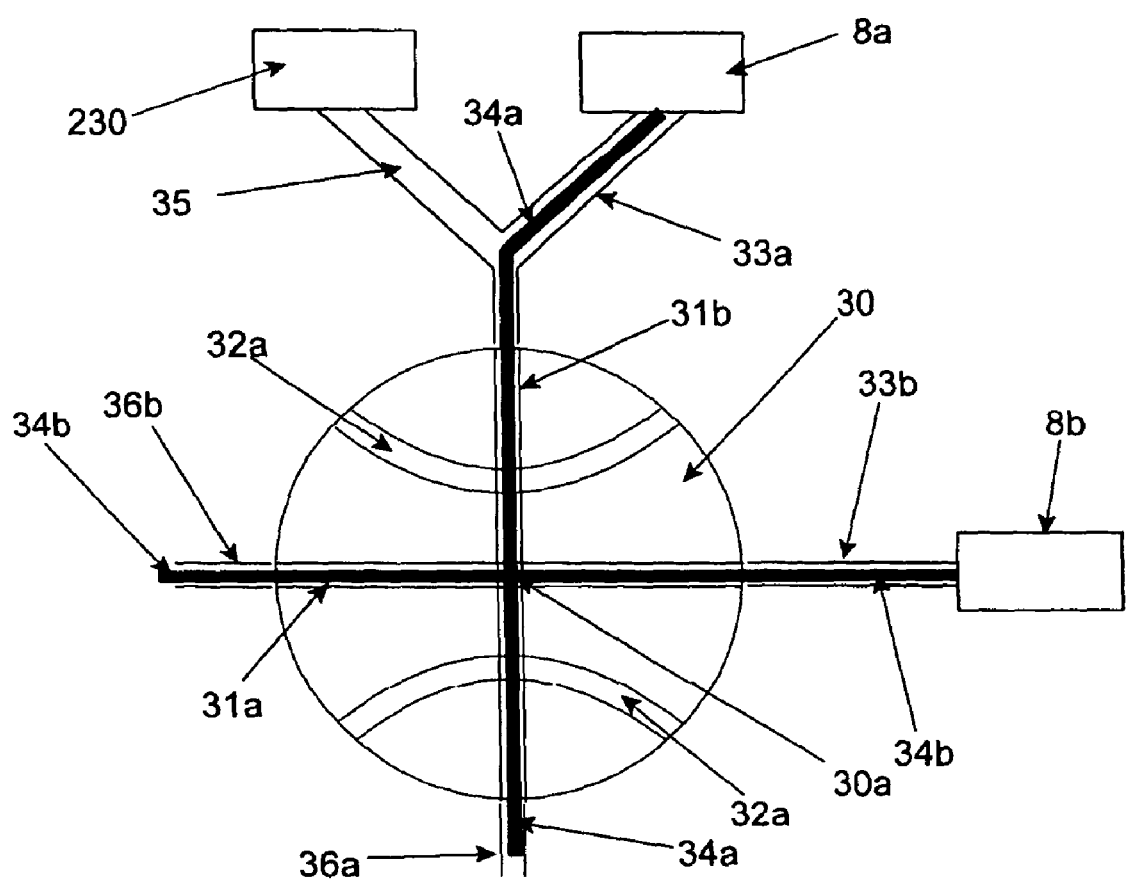
Figure 3B:
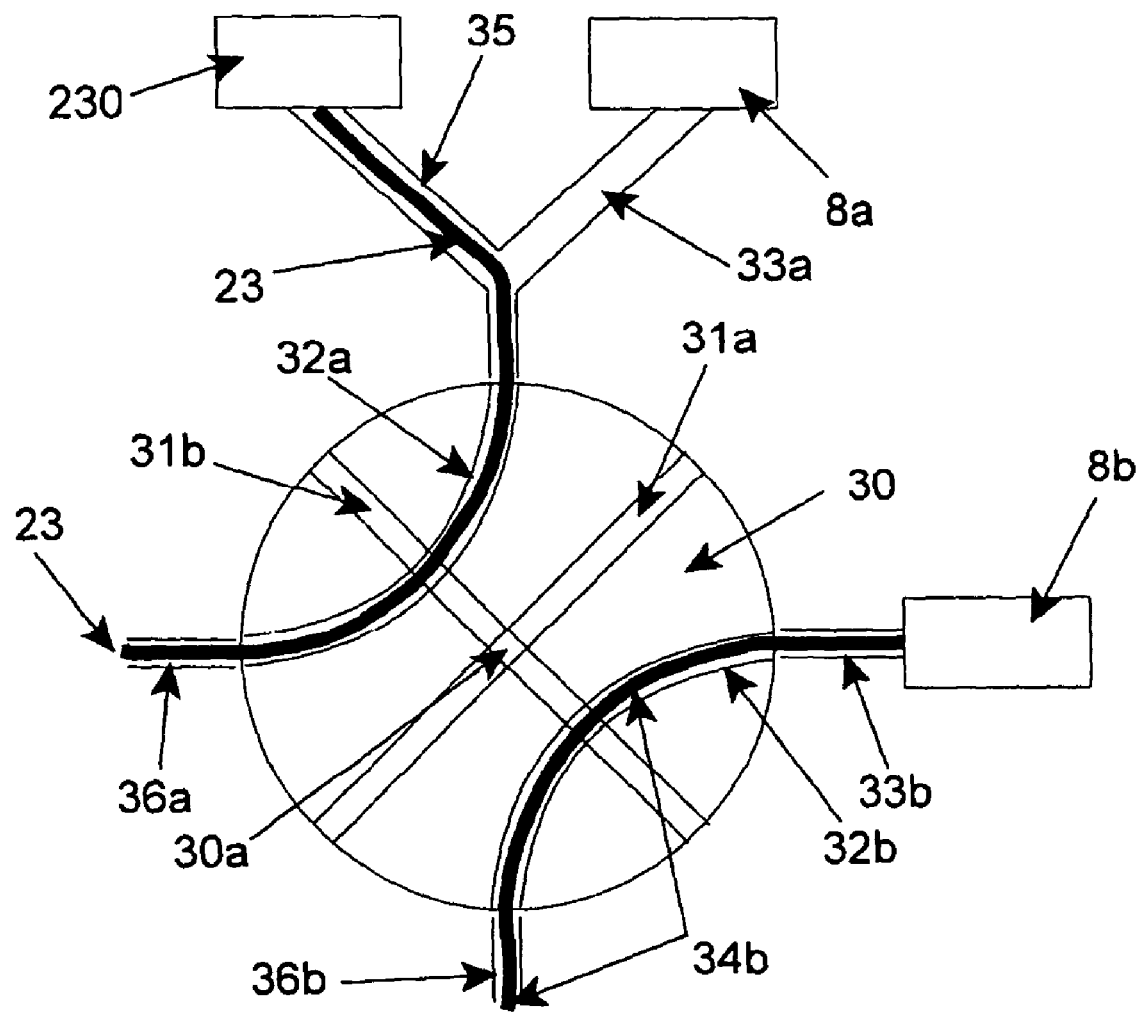
Figure 6A:
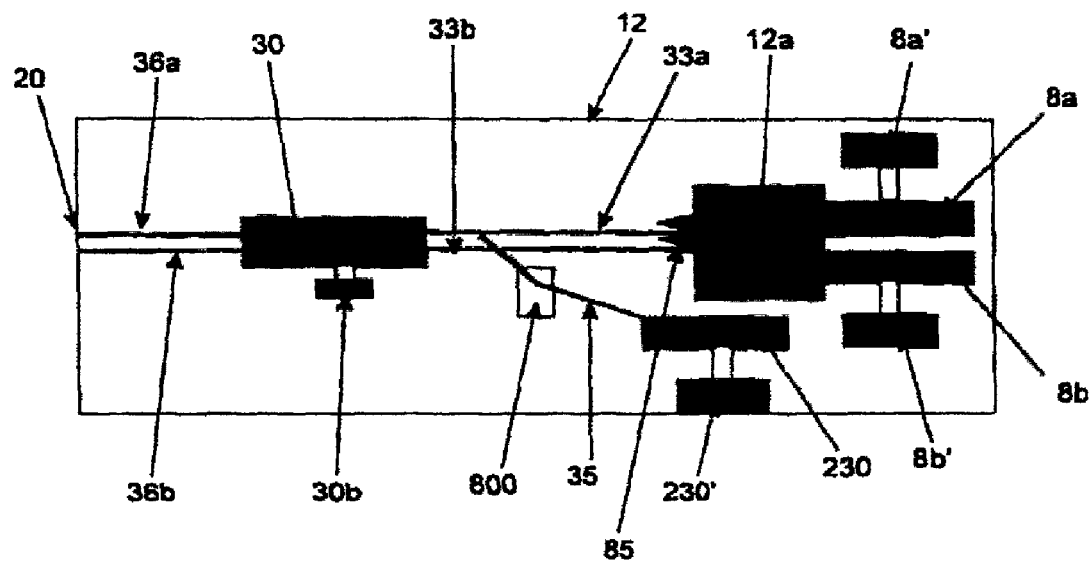
Figure 6B:
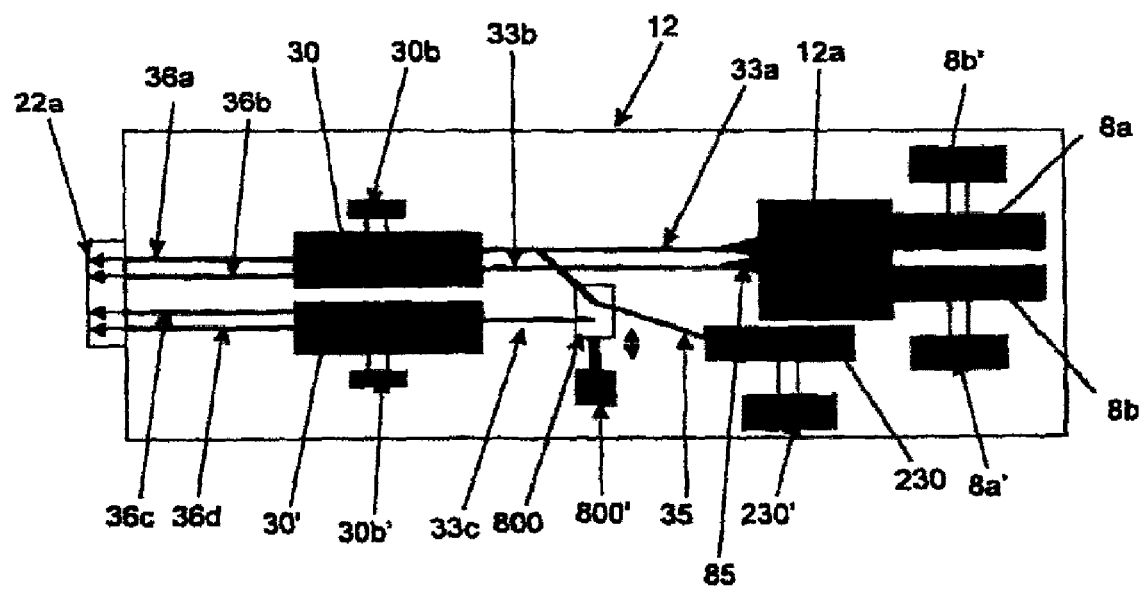
Figure 9:
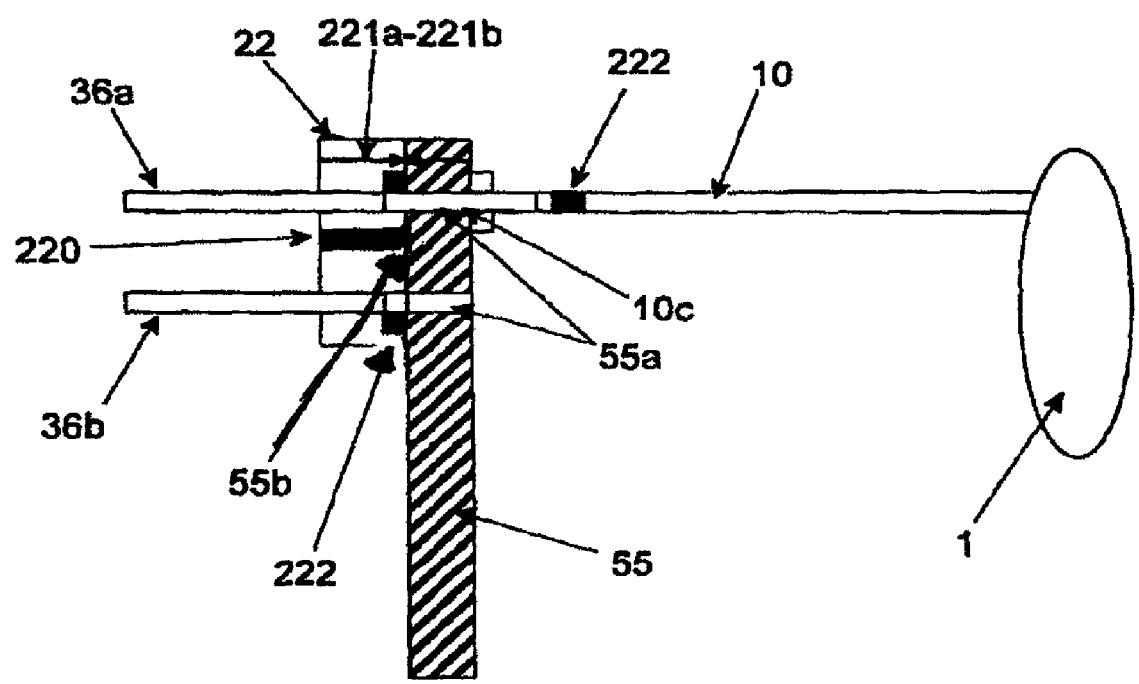
Figure 10A:
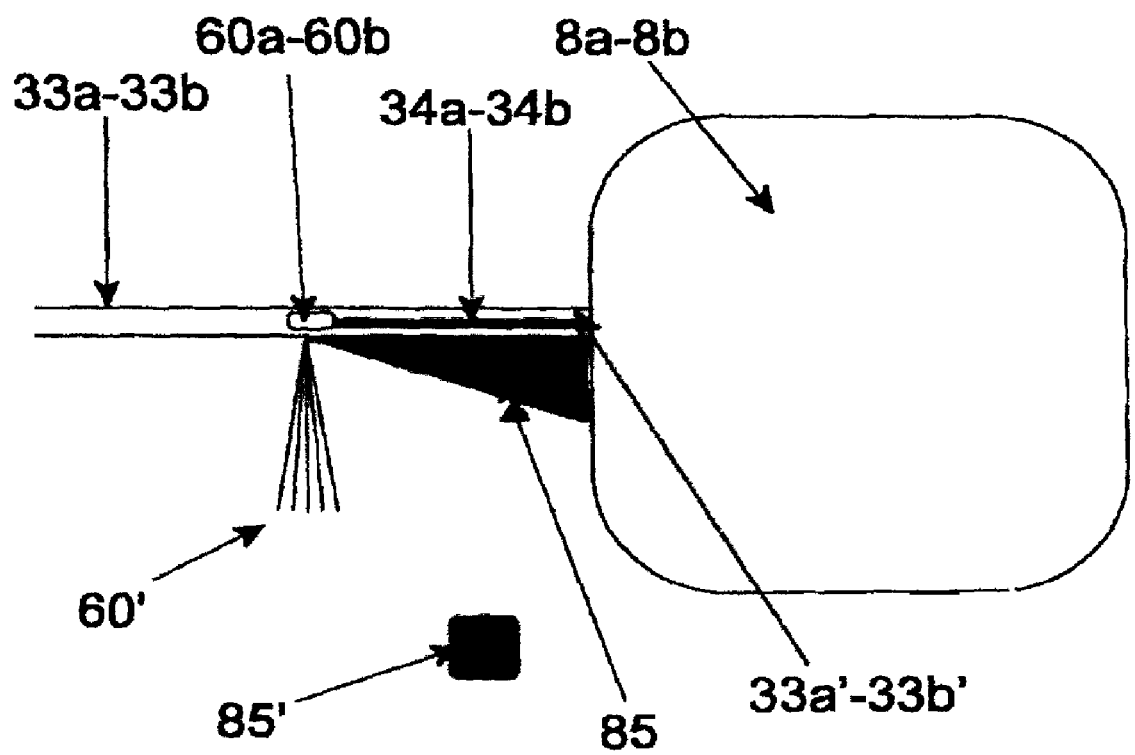
Figure 10B:
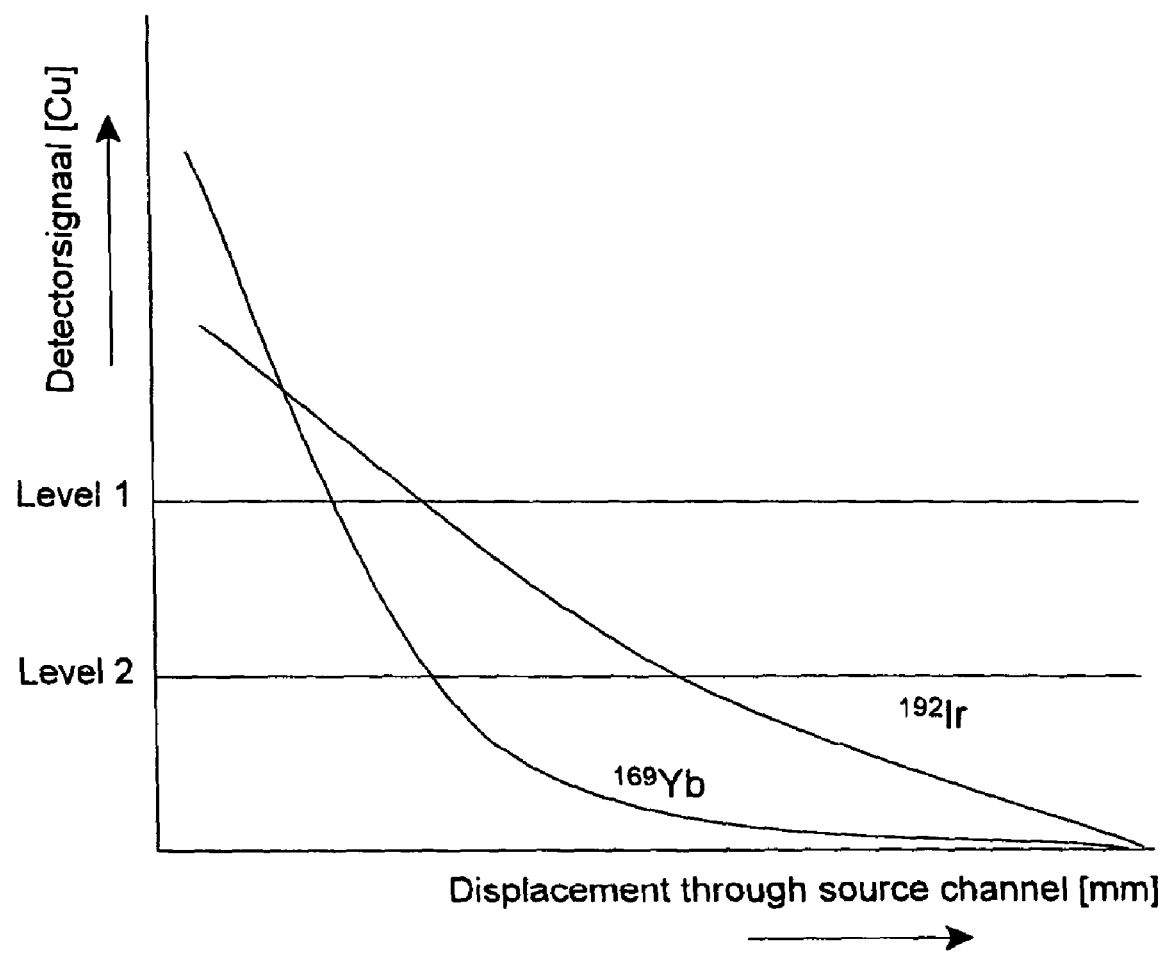

The invention shall now be described with reference to the accompanying drawings, which show:

FIG. 1 an apparatus according to the state of the art;

FIG. 2 an embodiment of an apparatus according to the invention;

FIGS. 3a-3b detailed but schematic views of the apparatus of FIG. 2;

FIGS. 4a-4b detailed but schematic views of another embodiment of the apparatus according to the invention;

FIGS. 5a-5b detailed but schematic views of another embodiment of the apparatus according to the invention;

FIGS. 6a-6b another embodiments of the apparatus according to the invention;

FIGS. 7a-7b and 8a-8b another embodiments of the apparatus according to the invention;

FIGS. 9 and 10a-10b yet another embodiments of the apparatus according to the invention.

For clarity reasons corresponding parts depicted in the drawings will be denoted with the same reference numeral in the following detailed description.

In FIG. 1 a specific embodiment of the apparatus according to the state of the art and described in EP 05076645.0 is disclosed. The treatment apparatus 12 comprises a treatment planning unit 12 as well as radiation delivery or drive means 8 comprising a transfer tube 20 connected to a robotic arm provided with a connection element 22, which can be brought in contact with the proximal end 10a of a selected treatment channel 10 which is inserted into a pre-selected target tissue 11, for example the prostate gland within the patient's body 1 using a template 5 separately connected to the patient's body.

The connecting element 22 is provided with a through bore extending into an insertion of a delivery channel being connected with radiation drive means 8. The movement of the robotic arm is monitored and operated until the connecting element 22 is brought in alignment and in contact with the template 5 and the exposed end 10a of the hollow needle 10. Subsequent a tracking wire (not shown) is guided through the delivery channel towards the hollow needle 10 interconnected with the connecting element 22. At the distal end of the tracking wire a tracking element is present, which is preferably an electromagnetic tracking element.

The displacement of the electromagnetic tracking element through the selected hollow needle 10 can be reconstructed using suitable means described in EP 05076645.0. The obtained information represents the actual orientation of the hollow needle 10, which reconstructed orientation or location is compared with the pre-planned orientations of the plurality of hollow needles 10-10'-etc. which are to be inserted into the patient's body upon performing the radiation treatment.

Subsequently the tracking wire with the tracking element is retracted from the hollow needle 10 into the treatment apparatus 8-12 and a guiding or source wire with at its distal end an energy emitting source (a HDR or LDR source) is advanced through the connecting element 22 and the hollow needle 10 for performing radiation therapy treatment.

Subsequent the guiding wire and the energy emitting source are retracted back into the treatment apparatus 8-12, the connecting element 22 is disconnected from the template 5/the needle 10 and brought in alignment with a further hollow needle 10' inserted at a different location inside the patient's body 1.

A first embodiment of the device of the invention is disclosed in FIG. 2, which device is capable of handling multiple energy emitting sources accommodated in the housing 12. In this embodiment two sources are used, but more than two sources can also be implemented. Each energy emitting source 60a-60b is mounted to a corresponding source wire 34a-34b and accommodated in a corresponding source channel 33a-33b and stored in a shielding 12a. The sources 60a-60b can be advanced and retracted through the device to and from the patient by means of suitable radiation drive means 8a-8b (displacement means).

As in the prior art of FIG. 1 the embodiment of FIG. 2 is provided with identifying means 230 comprising a tracking element 23a connected to a tracking wire 23 accommodated in a tracking channel 35 to correctly identify which one of the delivery channels 36a-36b is connected with one of the treatment channels 10 positioned in a patient's body 1.

Whereas the embodiment of FIG. 1 is provided with one delivery channel, which is connected using the robotic arm 20 in a stepwise manner with each of the implanted treatment channels 10-10'-etcetera, the robotic arm of the embodiment of FIG. 2 is provided with at least two delivery channels 36a-36b which are interconnected using the connecting element 22 of the robotic arm 20 with the template 55 in which multiple treatment channels or implant needles 10 are placed into the patient's body 1.

Therefore the embodiment of FIG. 2 is provided with at least two source channels 33a-33b each connected with corresponding energy emitting source delivery means 8a-8b which are safely mounted in the device 12 using a radiation shielding 12a. From the radiation drive means 8a-8b an energy emitting source 60a-60b (not depicted in this Figure, but in FIG. 8) can be advanced and retracted through the source channel 33a-33b using a suitable source wire 34a-34b. Likewise the identification means 230 comprise a tracking wire 23 accommodated in a tracking channel 35, which tracking wire is provided at its free distal end with a tracking element 23a.

For a proper operation of the device 12 of FIG. 2, so-called source channel connection means 30 are provided for properly interconnecting one or more of said source channels 33a-33b with one of said delivery channels 36a-36b. Furthermore the delivery channel connecting means 30 are arranged in it simultaneously connecting the tracking channel 35 with another one of said delivery channels 36a-36b.

In other words the device 12 according to the invention as depicted in FIG. 2 is capable of connecting only alternatively in the same connecting positions the tracking channel 35 with the two delivery channels 36a-36b and simultaneously connecting the two source channels 33a-33b with the two delivery channels 36a-36b and alternatively with two delivery channels 36a-36b after the checking procedure resulting a waiting time of the sources 60a-60b (not depicted in this Figure, but in FIG. 8).

In the FIGS. 3A and 3B a first embodiment of the delivery channel connecting means 30 is depicted. In the embodiment of FIGS. 3A and 3B the delivery channel connecting means are shaped as a disc-shaped element, which is rotatable about its longitudinal axis 30a and which disc 30 is provided with grooves 31a-31b; 32a-32b, wherein each groove is capable of interconnecting one of said delivery channels 36a-36b with either one of the source channels 33a-33b or tracking channel 35. As clearly depicted in FIGS. 3A and 3B at least two of said grooves 31a-31b are shaped as straight grooves, which cross in this embodiment each other in a perpendicular manner. In a further embodiment at least one of said grooves 32a-32b is shaped as a curved groove exhibiting preferably ¼-quarter curvature.

In a first operation condition as depicted in FIG. 3A the cylindrical-shaped connection element 30 is positioned in such manner that the straight groove 31a is interconnecting the source channel 33b of the radiation drive means 8b with the delivery channel 36b. This allows the advancement of the source wire 34b and the energy emitting source 60b (not depicted in this Figure, but in FIG. 8) accommodated in said radiation drive means 8b through the source channel 33b, the interconnecting groove or channel 31a towards the delivery channel 36b. Likewise the interconnecting groove or channel 31b interconnects the source channel 33a with the delivery channel 36a, allowing the advancement of the source wire 34a and the energy emitting source 60a (not depicted) from the radiation drive means 8a towards the delivery channel 36a.

The device of FIG. 2 is capable of connecting only alternatively in the same connecting positions the tracking channel with the two delivery channels and two source channels simultaneously and alternatively with two delivery channels during the checking procedure resulting a waiting time of the sources 60a-60b.

In FIG. 3B the delivery channel connecting means/cylindrical-shaped element 30 is rotated over 45□ around its longitudinal axis 30a bringing the two straight grooves 31a-31b out of line with one of the source channels 33a-33b and the delivery channels 36a-36b. However with the rotational displacement of the disc-shaped element 30, the curved grooves 32a-32b are now brought in alignment with either source channel 33a-tracking channel 35 (with delivery channel 36a) and the source channel 33b (with the delivery channel 36b).

In this operational condition the energy emitting source 60b (not depicted) of the radiation drive means 8b is now advanced using the source wire 34b through the source channel 33b towards the other delivery channel 36b. Simultaneously the tracking channel 35 has been interconnected with the other delivery channel 36a via the curved groove 32a allowing the advancement of the tracking wire 23 (with the tracking element 23a) with the delivery channel 36a.

In this operational condition one radiation treatment session can be performed using the radiation drive means 8b, whereas simultaneously a further treatment channel can now be identified using the tracking element 23a whilst inserting an energy emitting source until within the patient's body.

In FIGS. 7 and 8 another embodiment of the delivery channel connecting means are disclosed, now depicted with reference number 300. In this embodiment the delivery channel connecting means still comprise a rotatable connection element being rotatable allowed its longitudinal axis 300a and having an entrance end surface 301a and an exit end surface 301b. The embodiments of FIGS. 7 and 8 constitute a cylindrically-shaped element 300 with a circumferential surface 301c wherein multiple grooves are present extending substantially parallel to the longitudinal axis 300a.

Figure 7B:
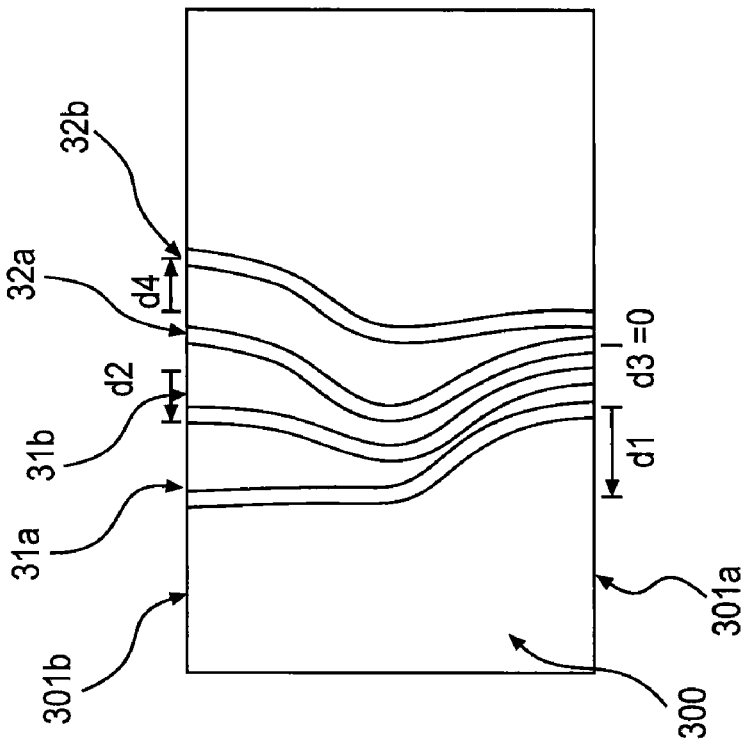
Figure 7A:
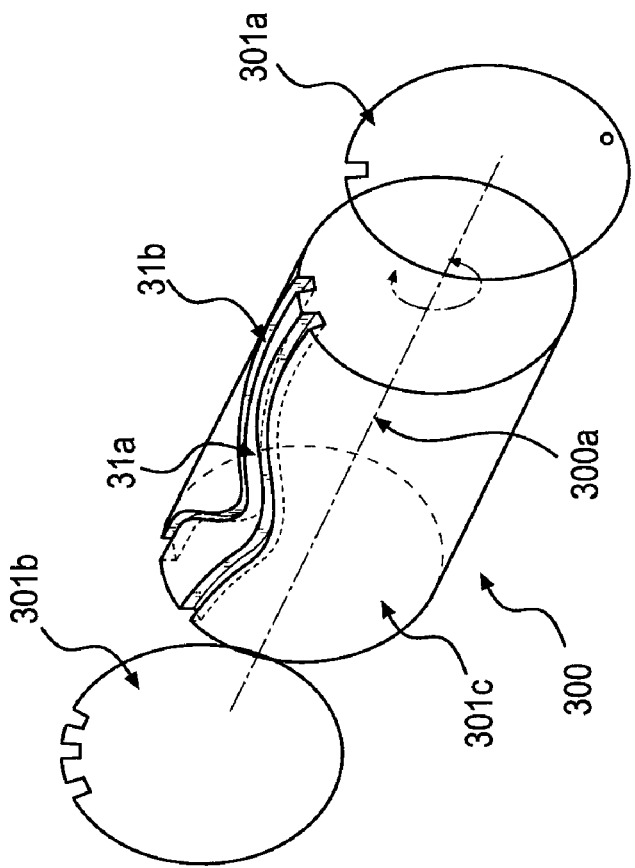

In the embodiment of FIG. 7A two longitudinally extending grooves 31a-31b are present, whereas in the embodiment of FIG. 7B four grooves 31a-31; 32a-32b are present. Upon rotation of the cylindrically-shaped channel connecting element 300 along its longitudinal axis 300a in one or more operational conditions the grooves 31a-31b; 32a-32b can be brought in alignment at their entrance end surface 301a with one of said source channels 33a-33b and tracking channel 35 whereas the grooves 31a-31b; 32a-32b can be brought in alignment at their exit end surface 301b with one of said delivery channels 36a-36d (see FIGS. 8A-8B).

As will be seen from the FIGS. 8A-8B the rotational orientation of the cylindrical channel connection element 300 allows the guidance of a source wire 34a-34b of tracking wire 23 from one of said source channels 33a-33b or tracking channel 35 towards one of said delivery channels 36a-36d thereby advancing the corresponding energy emitting source 36a-36b or tracking element 23a towards the intended treatment channel implanted into the patient's body and interconnected with the corresponding delivery channel 36a-36d.

Figure 4:
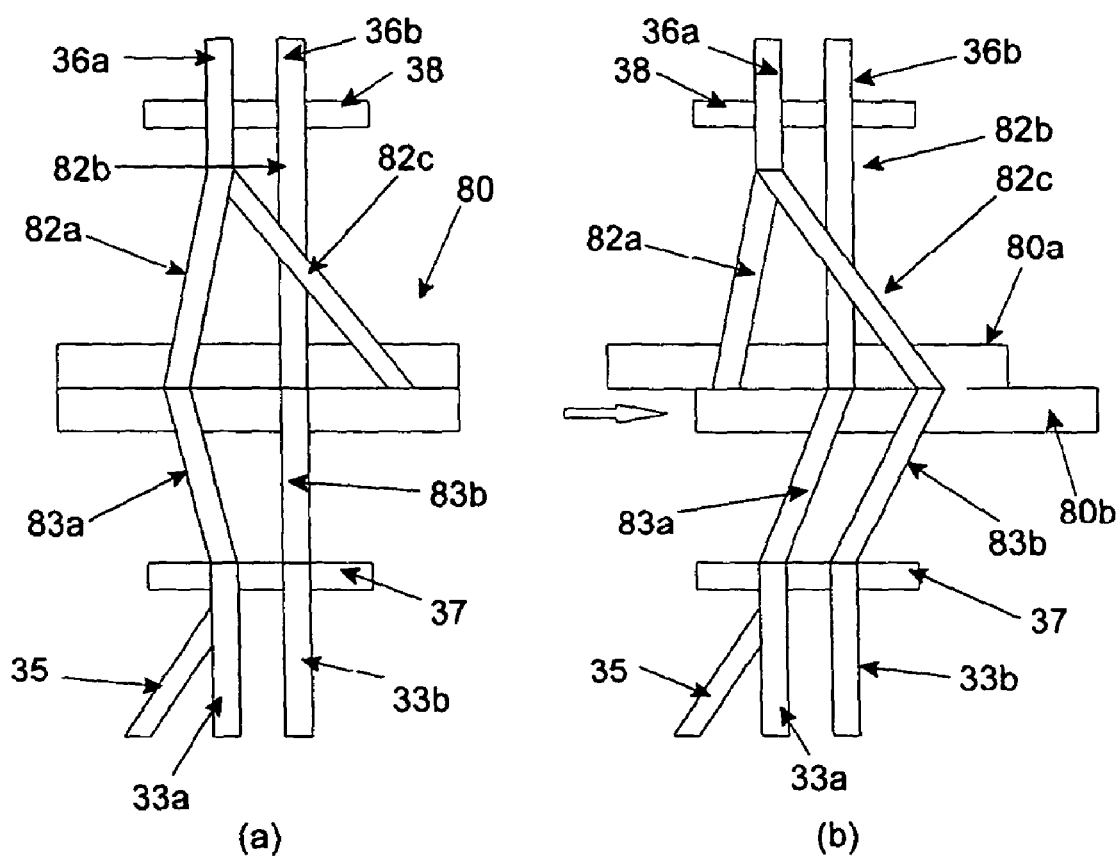
Figure 5:
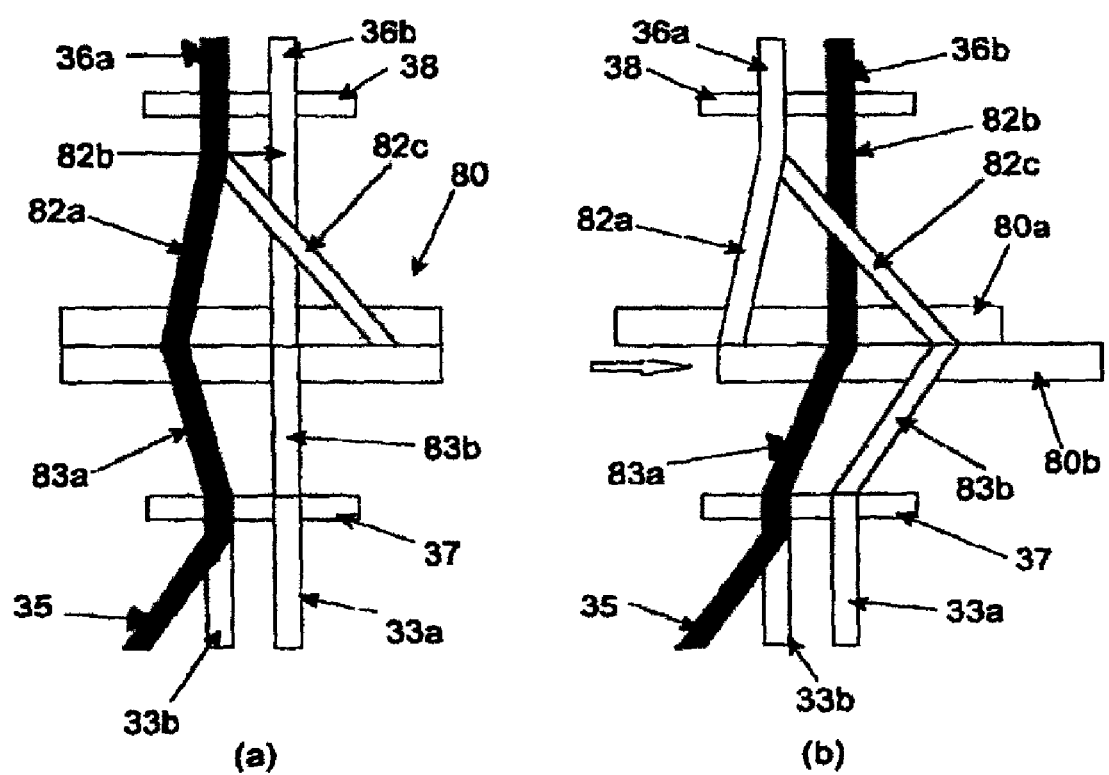

In the FIGS. 4 and 5 alternative embodiments of the delivery channel connecting means according to the invention are disclosed. In this embodiment the delivery channel connecting means are constructed as a shifting element 80, which can be displaced in a lateral direction (perpendicular to the orientation of the source channels 33a-33b and/or tracking channel 35). The shifting element 80 is provided with grooves or channels capable of interconnecting-depending on the lateral displacement of the shifting element, one of the delivery channels 36a-36b-etcetera with either one of the source channels 33a-33b or tracking channel 35. Shifting element 80 consists of two element parts 80a-80b, wherein the element part 80a is positioned in a fixed manner, and wherein the element part 80b is capable of lateral displacement relative to the fixed element part 80a. However it will be clear that in another embodiment the element part 80b can be positioned in a fixed manner whereas the other element part 80a is capable of lateral displacement.

The element part 80a is provided with—in this embodiment—three exit grooves or channels 82a-82b-82c, wherein the exit channels 82a-82c are connected via the connection block 38 with the delivery channel 36a, whereas the exit channel 82b is connected via the connection block 38 with the other delivery channel 36b. The shifting element part 80b is likewise provided with two entrance grooves or channels 83a-83b which are interconnected using the connection block 37 with the, here two source channels 33a-33b and one tracking channel 35.

In the FIGS. 4A-4B and 5A-5B four operation conditions are depicted, wherein in FIG. 4A the entrance channels 83a-83b are interconnected with the exit channels 82a-82b allowing the advancement of the energy emitting sources (not depicted) 60a-60b via the source channels 33a-33b to the delivery channels 36a-36b.

In the operational condition of FIG. 4B the shifting element part 80b is shifted in lateral direction (to the right) interconnecting the entrance channel 83b with the exit channel 82b (and the source channel 33a with the delivery channel 36b) as well as interconnecting the entrance channel 83b with the exit channel 82c (the source channel 33b with the delivery channel 36a). In this operational condition the interconnection between the source channels 33a-33b and the delivery channels 36a-36b has been shifted or switched in relation to the operational condition of FIG. 4A.

The operational condition of FIG. 5A (which corresponds with the condition of FIG. 4A) the tracking channel 35 is used to advance a tracking element from the identification means 230 (see FIG. 2) through the entrance channel 83a, the exit channel 82a towards the delivery channel 36a for the purpose of identifying the correct delivery channel 36a and the interconnected (not shown) treatment channel. In the operational condition of FIG. 5B (which corresponds with FIG. 4B) the tracking element 23a can be advanced via the treatment channel 35 towards the other delivery channel 36b, again for identifying purposes.

In FIGS. 6A and 6B two more embodiments of the device 12 according to the invention are depicted in a more schematic view but more or less having the same technical features as the embodiment of FIG. 2. The embodiments of FIGS. 6A and 6B have the additional feature of a further shifting element 800 being part of the delivery channel connecting means. Said further switching element 800 is a simplified version of the switching element 80 of FIG. 4-5 and comprises in the embodiment of FIG. 6A one entrance channel 83a connected with the tracking channel 35 and being connected with the switching elements 30-30'.

In the embodiment of FIG. 6B use is made of at least two energy emitting sources each contained in the shielding 12a and displaced by radiation drive means 8a-8b (as in the embodiment of FIG. 6A). Furthermore one tracking element 23a contained in identifying means 230 is used. However in this embodiment four delivery channels 36a-36d are used and interconnected with corresponding treatment channels implanted in the patient's body using the robotic arm 20 (of FIG. 2). In order to allow a proper selection of either one of said delivery channel 36a-36d with either one of the source channels 33a-33b and the tracking channel 35 two channel connection elements as disclosed in FIGS. 3A-3B (or FIGS. 4-5, 7-8) are used in combination with a shifting element.

In this FIG. 6B embodiment again a shifting element 800 of a simplified version of the switching element of FIG. 4-5 is used (as described in connection with FIG. 6A) having one entrance channel 83a connected with the tracking channel 35 and being connected with the switching elements 30-30'.

Both simplified switching elements 800 of FIGS. 6A-6B can be operated by the driving means 800'(for displacing in a transverse direction of the element part 80b) for interconnecting the tracking channel 35 with either one of the source channels 33a-33b-33c-33d (and hence with one of the switching elements 30-30'). Each switching element 30-30' can be likewise be operated using operation means 30b-30b' for example by rotating the disc-shaped switching element of FIG. 3A-3B or by rotating the cylindrical switching element of FIG. 7-8 or with the switching element of FIGS. 4-5. Each switching element 30-30' is used to select either one of the delivery channels 36a-36b or 36c-36d respectively.

With the embodiments of FIG. 6A-6B combined with the embodiments of FIGS. 3a-3b, FIGS. 4-5 or FIGS. 7-8 the two energy emitting sources 60a-60b (not depicted in this Figure but in FIG. 8) can be advanced through their respective source channels 33a-33b and tracking channel 35 in the direction to the delivery channels 36a-36b (36a-36b) wherein the delivery channel connecting means 30 are capable in alternatively to be connected with the delivery channels 36a-36d allowing the simultaneous and alternative insertion of two energy emitting sources 60a-60b (not depicted in this Figure but in FIG. 8) to either one of the delivery channels 36a-36b.

Simultaneously the tracking element 23a can be displaced to check in one connection position of the connecting element 22 (of the robotic arm 20) with the template 55 all delivery channels 36a-36d. First the delivery channels 36a-36b are checked/identified and thereafter in the same time when the sources 60a-60b are inserted into this checked delivery channels 36a-36b the tracking wire 23 moves after switching the switching element 80 into the delivery channels 36c-36d.

In FIG. 9 an embodiment is disclosed of the connection element 22 of the robotic arm 20 which connection element is adapted to be brought in engagement with a template 55 to which the multiple hollow treatment channels 10 are connected. The template 55 is thereby provided with multiple grooves or bores 55a in which multiple treatment channels 10 (implant needles) can be accommodated using suitable coupling parts 10c, which treatment channels 10 are implanted into a patient's body 1.

The connection element 22 is detachable from the template 55 allowing the stepwise interconnection of the robotic arm 20 provided with at least two delivery channels 36a-36b with corresponding implanted treatment channels 10. Therefore it is avoided that the patient 10 is interconnected with the device 12 according to the invention via a large number of delivery channels equal to the number of implanted treatment channels (implant needles) 10. The patient is only discomforted with a number of implanted treatment channels 10 which are interconnected with a template preferably fixed on the treatment table. The template 55 in turn is coupled to the robotic arm 20 in such manner that a limited number of treatment channels 10 are interconnected with a corresponding number of delivery channel 36a-36b during one treatment session and can be completely unconnected if necessary without human (users) intervention. The latter is very advantageous in special situations of imaging during the treatment session.

In order to allow a proper engagement between the robotic arm 20/connection element 22 with the template 55 coupling elements 220-55b are present on both the connection element 22 and the template 55. The coupling elements consists of a electromagnet 220 present on the robotic arm 20, which electromagnet 220 interacts with suitable magnetic contact elements positioned at specific locations on the template 55 as indicated with reference numeral 55b. When the connection element 22 is properly connected with the template 55 the electromagnet 220 will make a proper magnetic contact with a corresponding magnetic contact element 55b resulting in a fixed coupling.

Furthermore the robotic arm 20 can be provided with multiple sensing elements 221a-221b for sensing the presence of a inserted treatment channel into the template 55. In order to allow a proper engagement between the robotic arm 20/coupling element 22 with the template 55 the sensing elements 221a-221b are present on both the connection element 22 and the template 55 and may be constructed as a pair of a light emitting element (diode) 221a-221b and a light receiving element 221b-221a. A proper interaction of a pair of said sensing elements 221a-221b with the inserted connecting element 22 into the template of the treatment channel will result in a proper signal generated and sent to the control means of the device 12.

As long as the coupling element 22 is not brought in a proper engagement with the template 55 no interaction will occur between the sensing elements 221a-221b and no signal will be sent to the control means of the device 12 and therefore both the identification means 230 and the radiation drive means 8a-8b are not activated thereby avoiding the accidental advancement of the tracking element and/or one of more energy emitting sources through the delivery channels to the free, open connection element 22 resulting in hazardous, unsafe situations, such as the dangerous exposure to a radiation of the environment by the unintended advancement of the energy emitting sources 60a-60b.

Once a proper engagement between the robotic arm 20/coupling element 22 has been established with the template 55, said engagement is maintained by the electromagnet 220 and the magnetic contact element 55b.

Also disclosed in FIG. 9 are radiofrequency identification elements 222 being part of the identifying means. Each radiofrequency identification element 222 is mounted on one of said n hollow treatment channels 10 or on the template 55 near one of the delivery channels. A radiofrequency identification element 222 (or RFID) near one of said treatment channels 10 can be controlled or triggered by the tracking element 23a passing by during its displacement with the tracking wire 23 through the device 12, one of said delivery channels 36a-36d towards one of said interconnected treatment channels 10. Hereto the tracking element 23a should exhibit some kind of magnetic activity, e.g. through the ferromagnetic properties of the tracking element 23a.

The passing by of the tracking element 23a will change the radiofrequency emission properties of the RFID 222. In one embodiment the RFID 222 is usually in a so-called 'off' or 'silent' or 'low energy' state and will be switch 'on' by said tracking element 23a passing by during its displacement through the corresponding hollow treatment channel 10. In another embodiment the RFID 222 is continuously emitting electromagnetic energy and the amount of said electromagnetic energy being emitted changed by said tracking element 23a passing by. In yet another embodiment the already emitting RFID 222 is completely switched off by said tracking element passing by.

In all three situations the changes in the radiofrequency being emitted (from 'off' to 'on', from high to low, or from 'on' to 'off') can be detected with suitable means known in the art and used for identifying purposes by the identifying means 230.

In a further embodiment the identification means can also be partly incorporated in the tracking element 22. In that embodiment use is made of accelerometer sensors and/or of gyroscope sensors. The accelerometer measures the acceleration of the tracking element 23a during displacement through the delivery channel in a certain direction, whereas the gyroscope sensor converts acceleration and change in rotation into signals.

With this embodiment a new proper positioning of the tracking element is accomplished improving the accuracy of the radiation treatment and avoiding treatment errors due to incorrect interconnections of the delivery channels with one or more treatment channels.

In FIGS. 10A and 10B a further embodiment is disclosed of a specific feature of the device according of the invention wherein energy emitting source identifying means 85-85' are present at each connection between a source channel 33a-33b with the radiation shielded storage of the energy emitting sources of the radiation drive means 8a-8b. The energy emitting source identifying means comprises a wedge-shaped element 85 mounted in the near facility of the exit opening 33a'-33b' of each radiation drive means 8a-8d.

Usually the energy emitting sources 60a-60b used in the device according to the invention, are considered continuously emitting sources, for example radioactive sources (HDR- or PDR-sources). In order to avoid a possible incorrect activation of one of said radiation drive means 8a-8b-etc. and therefore the use of an incorrect energy emitting source for the intended radiation treatment as preplanned the radiation 60' emitted by the energy emitting source 60a-60b is directly monitored upon leaving the radiation shielded storage of the radiation drive means 8a-8b.

To this end the wedge-shaped element 85a is manufactured from a radiation absorbing material, for example lead, resulting a dose distribution detected by the radiation detector 85' as depicted in FIG. 10B. From the detected dose distribution generated during the displacement of the energy emitting source 60a-60d upon leaving the radiation drive means 8a-8b through the source channel 33a-33b along the wedged-shaped shielding element 85 a proper identification of the energy characteristics of the advanced source 60a-60b. With this measuring method an early identification of the energy emitting source 60a-60b being advanced through the source channel 33a or 33b is obtained allowing an early and proper correction in the event that the incorrect source 60a-60b is being advanced through the device 12 towards the robotic arm 22 thereby avoiding an incorrect administering of energy to the patient to be treated as well as avoiding hesitate situations to the environment (and the patient).

The invention claimed is:

1. An apparatus for effecting radiation treatment on a pre-selected anatomical portion of an animal body comprising:
   a group of n treatment channels configured to be inserted at one or more pre-planned positions in the pre-selected anatomical portion;
   a group of m delivery channels that are interconnected with a corresponding number m of the group of n treatment channels with m being 2 or more and n being 3 or more;
   an identifying element configured to identify which one of the group of m delivery channels is connected with which one of the group of n treatment channels, the identifying element including a tracking element disposed in a tracking channel, wherein the tracking element is configured to be displaced from the tracking channel through each of the interconnected m delivery channels and m treatment channels;
   a storage element configured to store one of a plurality of k energy emitting sources in a respective one of a plurality of source-channels, wherein k≦m;
   at least one drive element configured to temporarily insert a respective one of the plurality of k energy emitting sources from a corresponding one of the plurality of source-channels through a corresponding one of the interconnected m delivery channels and m treatment channels towards one of the pre-planned positions in the pre-selected anatomical portion;
   an arm configured to couple at least one of the group of m delivery channels with at least one of the group of n treatment channels, wherein the arm includes a coupling element having an arrangement in which one of the plurality of k energy emitting sources and the tracking element can be inserted alternatively or simultaneously through the m delivery channels towards the interconnected m treatment channels and m delivery channels after the m delivery channels and m treatment channels have been checked by the identifying element.

2. An apparatus according to claim 1, further comprising a connecting element, wherein the connecting element includes a cylindrical shaped element having a longitudinal axis, wherein the cylindrical shaped element is rotatable—about the longitudinal axis, and wherein the cylindrical shaped element includes a plurality of grooves, each groove of the plurality of grooves interconnecting one of the group of m delivery channels with either one of the plurality of source-channels or the tracking channel.

3. An apparatus according to claim 2, wherein at least two of the plurality of grooves are shaped as straight grooves.

4. An apparatus according to claim 3, wherein the straight grooves cross each other in a perpendicular manner.

5. An apparatus according to claim 2, wherein at least one of the plurality of grooves is shaped as a curved groove.

6. An apparatus according to claim 5, wherein the curved groove extends along approximately a quarter of a circumference of the cylindrical shaped element.

7. An apparatus according to claim 2, wherein the plurality of grooves are provided in an end face of the cylindrical shaped element, the end face extending perpendicularly to the longitudinal axis of the cylindrical shaped element.

8. An apparatus according to claim 2, wherein the plurality of grooves are provided in a circumferential surface of the cylindrical shaped element, the circumferential surface extending substantially parallel to the longitudinal axis of cylindrical shaped element.

9. An apparatus according to claim 1, further comprising a connecting element, wherein the connecting element includes a shifting element configured to displace in a lateral direction, wherein the shifting element includes a plurality of grooves interconnecting one of the m delivery channels with either one of the plurality of source-channels or the tracking channel.

10. An apparatus according to claim 9, wherein each of the plurality of grooves is shaped as a straight groove.

11. An apparatus according to claim 9, wherein each of the plurality of grooves has an inclined configuration when the shifting element is displaced in the lateral direction.

12. An apparatus according to claim 1, wherein the arm includes the group of m delivery channels and has a coupling element at a free end of the arm.

13. An apparatus according to claim 12, wherein the coupling element is configured to engage a template connected to the group of n treatment channels.

14. An apparatus according to claim 13, wherein the arm includes at least one activatable first sensing element on the coupling element.

15. An apparatus according to claim 14, wherein the template includes a second sensing element, and wherein the first sensing element and the second sensing element include a light emitting element and a light receiving element, respectively.

16. An apparatus according to claim 12, wherein the arm includes at least one electromagnet on the coupling element, the electromagnet configured to couple the coupling element to a template during treatment.

17. An apparatus according to claim 1, wherein k=2 and m=4.

18. An apparatus according to claim 1, wherein the identifying element further includes a plurality of radiofrequency identification elements, each of the radiofrequency identification elements being mounted to a respective one of the group of n treatment channels, and wherein each of the radiofrequency identification elements is operated by the tracking element as the tracking element is displaced through the respective one of the group of n treatment channels.

19. An apparatus according to claim 18, wherein each of the plurality of radiofrequency identification elements is configured to be activated on when the tracking element is displaced through the respective one of the group of n treatment channels.

20. An apparatus according to claim 18, wherein each of the plurality of radiofrequency identification elements is configured to emit electromagnetic energy and wherein the amount of electromagnetic energy that is emitted by each of the plurality of radiofrequency identification elements changes as the tracking element is displaced through the respective one of the group of n treatment channels.

21. An apparatus according to claim 20, wherein each of the plurality of radiofrequency identification elements is configured to be deactivated off when the tracking element is displaced through the respective one of the group of n treatment channels.

22. An apparatus according to claim 1, wherein the tracking element is provided with at least one of a gyroscope sensor and an accelerometer sensor.

23. An apparatus according to claim 1, further comprising a plurality of energy emitting source identifying elements, wherein each of the plurality of energy emitting source identifying elements is mounted near a respective one of the plurality of source-channels and is configured to identify energy characteristics of a respective one of the plurality of k energy emitting sources as the respective one of the plurality of k energy emitting sources is displaced through the respective one of the plurality of source-channels.

24. An apparatus according to claim 23, wherein each one of the plurality of energy emitting source identifying elements includes an energy shielding element and an energy detecting element, the energy shielding element at least partly shielding the plurality of source-channels from the energy detecting element.

25. An apparatus according to claim 24, wherein the energy shielding element is constructed as a wedge shaped element.

26. A method for effecting radiation treatment on a pre-selected anatomical portion of an animal body comprising the steps of:
 inserting a plurality of treatment channels at one or more positions in the pre-selected anatomical portion;
 connecting the plurality of treatment channels to a corresponding number of connecting positions on a fixed positioned connecting template;
 connecting a plurality of delivery channels to a corresponding number of connecting positions of the template;
 wherein the step of connecting the plurality of delivery channels to the corresponding number of connecting positions of the template includes selectively and alternatively connecting the plurality of delivery channels with a corresponding number of the plurality of treatment channels;
 displacing a tracking element disposed in a tracking channel through each of the plurality of delivery channels and the corresponding number of the connected plurality of treatment channels; and
 inserting a plurality of energy emitting sources each through a respective one of the plurality of delivery channels and treatment channels towards one or more positions in the pre-selected anatomical portion.

* * * * *